US00PP34050P2

(12) United States Plant Patent
Lim

(10) Patent No.: US PP34,050 P2
(45) Date of Patent: Mar. 22, 2022

(54) ***HIBISCUS* PLANT NAMED 'ALTICEMELON'**

(50) Latin Name: *Hibiscus rosa-sinensis*
Varietal Denomination: ALTICEMELON

(71) Applicant: Altman Specialty Plants, Inc, Vista, CA (US)

(72) Inventor: Peter Lim, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/356,860

(22) Filed: Jun. 24, 2021

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ... A01H 5/02; A01H 5/00; A01H 6/60; A01H 6/608
See application file for complete search history.

*Primary Examiner* — June Hwu
(74) *Attorney, Agent, or Firm* — Cassandra Bright

(57) ABSTRACT

A new and distinct cultivar of *Hibiscus* plant named 'ALTICEMELON' is disclosed, characterized by large white and pink blooms with having a dark central blotch. Plants are compact with glossy foliage and prolific blooming. The new variety is a *Hibiscus*, typically produced as an ornamental plant.

1 Drawing Sheet

Latin name of the genus and species: *Hibiscus rosa-sinensis*.

Variety denomination: 'ALTICEMELON'.

BACKGROUND OF THE INVENTION

The new *Hibiscus* cultivar is a product of a planned breeding program conducted by the inventor, Peter Lim. The objective of the breeding program was to produce vigorous *Hibiscus rosa-sinensis* cultivars with healthy foliage. The cross resulting in this new variety was made Jun. 25, 2014.

The seed parent is the unpatented *Hibiscus rosa-sinensis* 'Rising Star'. The pollen parent is the unpatented variety *Hibiscus rosa-sinensis* 'Volcano'. The new variety was identified and selected as a potentially interesting selection in September of 2016. Selection was made at a commercial nursery in Vista, Calif.

Asexual reproduction of the new cultivar 'ALTICEMELON' was first performed on Sep. 25, 2016 in Vista, Calif., by vegetative cuttings. Subsequent propagation has shown that the unique features of this cultivar are stable and reproduced true to type in successive generations.

SUMMARY OF THE INVENTION

The cultivar 'ALTICEMELON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTICEMELON'. These characteristics in combination distinguish 'ALTICEMELON' as a new and distinct *Hibiscus* cultivar:

1. White and pink bi-colored flowers with noticeable white veins and a dark central blotch.
2. Large flower size.

3. Prolific blooming.
4. Compact growth habit.
5. Glossy foliage.

PARENT COMPARISONS

Plants of the new cultivar 'ALTICEMELON' are similar to the seed parent 'Rising Star', in most horticultural characteristics. However, characteristics of the new cultivar differ in the following:

1. The new variety has a white and pink flower, the seed parent has a yellow flower.

Plants of the new cultivar 'ALTICEMELON' are similar to the pollen parent 'Volcano', in most horticultural characteristics. However, characteristics of the new cultivar differ in the following:

1. Flowers of the new variety have more petals than flowers of the pollen parent.

COMMERCIAL COMPARISON

Plants of 'ALTICEMELON' are similar in some horticultural characteristics to the variety *Hibiscus* 'Loving Lady', unpatented. The new variety, however, differs in the following:

1. Flowers of 'ALTICEMELON' are smaller than flowers of 'Loving Lady'.
2. Plants of 'Loving Lady' have a taller growth habit than 'ALTICEMELON'.
3. Flowers of 'ALTICEMELON' are white and pink, while flowers of 'Loving Lady' are red with a white edge.

Plants of 'ALTICEMELON' are similar in some horticultural characteristics to the variety *Hibiscus* 'Strawberry Cream', unpatented. The new variety, however, differs in the following:

1. Flowers of 'ALTICEMELON' are smaller than flowers of 'Strawberry Cream'.

2. Plants of 'Strawberry Cream' have a taller growth habit than 'ALTICEMELON'.
3. Flowers of 'ALTICEMELON' are white and pink, with white veins, while flowers of 'Strawberry Cream' are white with a pink eye.

BRIEF DESCRIPTION OF THE PHOTOGRAPH

The accompanying photograph illustrates in full color typical flowers of 'ALTICEMELON' from a plant grown outdoors at a commercial nursery in Vista, Calif. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'ALTICEMELON' plant. The growing temperature ranged from about 7° C. to 30° C. during the day and from about 5° C. to 12° C. during the night. No artificial light, photoperiodic treatments were given to the plants. Measurements and numerical values represent averages of typical plant types.

Botanical classification: *Hibiscus rosa-sinensis* 'ALTICEMELON'.

PROPAGATION

Typical method: Hardwood stem cuttings.

Root description: Roots are fine, fibrous and well branched. Tan/brown in color, not effectively measured with a color chart.

PLANT

Plant type: Tender, woody flowering shrub.
Age of plant described: Approximately 2 years old.
Growth habit: Compact.
Height: 81 cm.
Plant spread: 55 cm.
Branching characteristics: 2 to 3 breaks from a pinch, occurring at acute angles.
Length of primary lateral branches: 20 to 35 cm.
Quantity of lateral branches: About 8 to 11.
Characteristics of primary lateral branches:
- *Diameter.*—9 mm.
- *Color.*—New growth near RHS Greyed-Purple 187A, mature growth near RHS Greyed-Green 197A, streaked Greyed-Purple 183A.
- *Texture.*—New growth very slightly hirsute, mature branches striated.

Internode length: Average 3 cm.

FOLIAGE

Leaf:
- *Arrangement.*—Alternate.
- *Quantity.*—Approximately 20 per branch.
- *Average length.*—11 to 12 cm.
- *Average width.*—10 cm.
- *Shape of blade.*—Broad ovate to nearly cordate.
- *Apex.*—Acute.
- *Base.*—Obtuse.
- *Margin.*—Crenate.
- *Texture of top surface.*—Glabrous.
- *Texture of bottom surface.*—Glabrous.
- *Color.*—Young foliage upper side: RHS Green 137A. Young foliage under side: RHS Green 137B. Mature foliage upper side: RHS Green 139A. Mature foliage under side: RHS Green 137B.
- *Venation.*—Type: Pinnate. Venation color, upper side: RHS Green 143C. Venation color, under side: RHS Yellow-Green 144B.
- *Petiole.*—Length: 5 to 7 cm. Diameter: 3 mm. Color: Upper side: Near RHS Greyed-Purple 187A, flushed Greyed-Purple N187A. Under side: Near RHS Green 137A, heavily flushed Greyed-Purple 187A. Texture: All surfaces roughly pubescent.
- *Stipule.*—Shape: Narrow deltoid. Length: 5 to 7 mm. Width: 3 mm. Color: Upper side: Near RHS Green 137D. Upper side: Near RHS Green 143C. Texture: Slight rough pubescence.

FLOWER

Natural flowering season: Late Spring through Summer.
Flower type and habit: Solitary, rotate.
- *Single, double, multiplex.*—Single.
- *Petals overlapping.*—Strongly overlapping.

Rate of flower opening: 1 to 2 days from bud to fully opened flower.
Flower longevity on plant: 1 to 2 days.
Persistent or self-cleaning: Self-cleaning.
Bud:
- *Shape.*—Ovate.
- *Length.*—5 cm.
- *Diameter.*—2.2 cm.
- *Color.*—RHS Yellow-Green 145C, lightly flushed Red 51C.

Flower size:
- *Diameter.*—14 cm.
- *Depth.*—9 cm.

Petals:
- *Quantity.*—5.
- *Arrangement.*—Whorled, overlapping.
- *Length.*—8 cm.
- *Width.*—8 cm.
- *Shape.*—Obovate.
- *Apex.*—Obtuse rounded with shallow ruffles.
- *Base.*—Broad attenuate.
- *Margin.*—Entire, moderate ruffling.
- *Texture, upper and lower surfaces.*—Smooth, rugose.
- *Incision.*—Absent.
- *Color.*—When opening, upper surface: RHS Red 49D, basal blotch (forming flower eye) Red-Purple 61C flushed N57B, covering approximately 80% of petal surface. Lowermost basal blotch near Red-Purple 61A flushed Greyed-Purple 187C. When opening, lower surface: RHS 49D, margins near Yellow-Orange 18D. Fully opened, upper surface: RHS White N155C, basal blotch (forming flower eye) Red-Purple 61C flushed N57B, covering approximately 50% of petal surface. Lowermost basal blotch near Red-Purple 61A flushed Greyed-Purple 187C. Veins through central blotch near White N155D. Fully opened, lower surface: RHS Yellow-Orange 18D, large central flush near Red 55D. Ratio of basal blotch/eye to petal size: About 30% of petal blade with darkest blotch. Feathering color: RHS Red-Purple 61C. Feathering size: Moderate about 10 to 20 mm.

Sepals:

*Quantity.*—5.

*Length.*—2.0 cm.

*Width.*—2 cm.

*Shape.*—Narrow, deltate.

*Margin.*—Entire.

*Apex.*—Acute.

*Base.*—Fused.

*Color.*—Upper surface: RHS Yellow-Green 144B. Lower surface: RHS Green 143B.

*Texture.*—Glabrous, all surfaces.

Epicalyx:

*Quantity of bracts.*—8 to 10.

*Bract length.*—1.2 cm to 2 cm.

*Bract width.*—3 mm.

*Bract shape.*—Lanceolate.

*Bract margin.*—Entire.

*Color.*—Upper surface: RHS Green 137A. Lower surface: Near RHS Green 138A.

*Texture.*—Glabrous all surfaces.

Peduncles:

*Length.*—4.5 cm.

*Diameter.*—3 mm.

*Angle.*—Approximately 45° to the lateral branch.

*Strength.*—Very strong.

*Texture.*—Pubescent.

*Color.*—RHS Yellow-Green 144B.

Fragrance: None.

REPRODUCTIVE ORGANS

Stamens:

*Number.*—About 60.

Anthers:

*Shape.*—Irregular sphere.

*Length.*—About 2 mm.

*Color.*—Near RHS Yellow-Orange 15A.

*Pollen color.*—Near RHS Yellow-Orange 15A.

*Pollen amount.*—Scant.

Pistil:

*Number.*—1.

*Length.*—10 cm.

*Style.*—Length: 9 cm. Color: Lower section near Red 53A, mid-section near Red-Purple N57B, upper section near Red 49C. Iridescent throughout.

*Stigma.*—Shape: Peltate. Color: Near RHS Yellow-Orange 15B.

*Ovary color.*—Near RHS Yellow-Green 154D.

OTHER CHARACTERISTICS

Seeds: Capsule, typically about 1 cm in diameter and length. Pubescent, colored near RHS Grey-Brown 199B. Moderately abundant lightly pubescent seed.

Disease/pest resistance: Neither resistance nor susceptibility to normal diseases and pests of *Hibiscus rosa-sinensis* have been observed.

Temperature tolerance: USDA Zones 8 through 11.

What is claimed is:

1. A new and distinct cultivar of *Hibiscus* plant named 'ALTICEMELON' as herein illustrated and described.

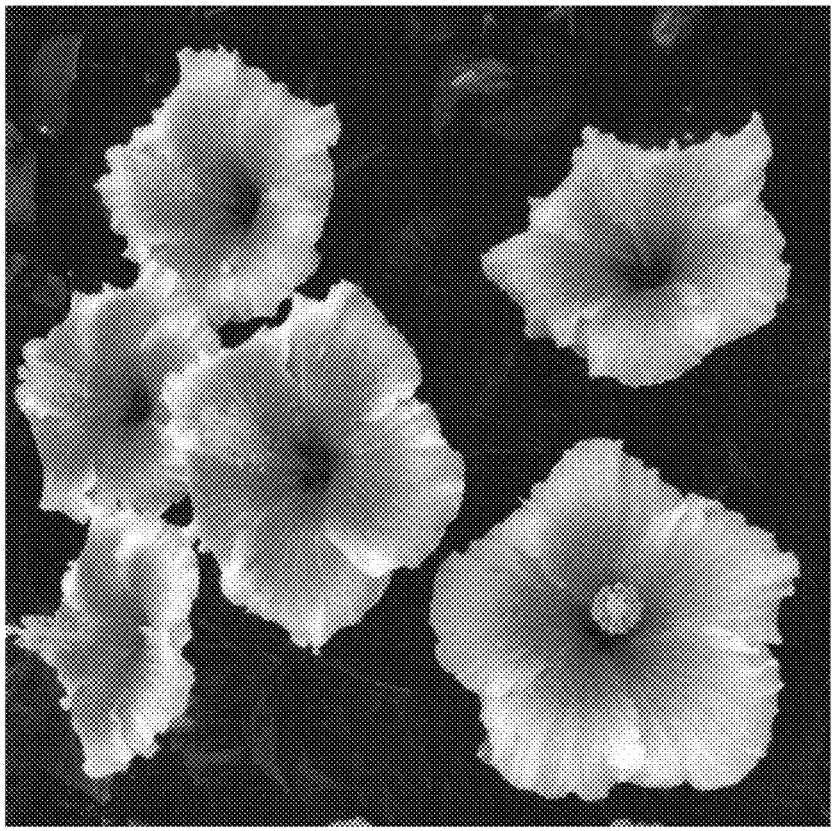

* * * * *